(12) United States Patent
Ackerman

(10) Patent No.: US 8,226,630 B2
(45) Date of Patent: Jul. 24, 2012

(54) METHOD OF USING PREFILLED, SINGLE DOSE, ONE TIME USE SELF-DESTRUCTING, AUTO-DISABLING SAFETY SYRINGE

(76) Inventor: Timothy Ackerman, Bradenton, FL (US); Robert S. Ackerman, legal representative, Bradenton, FL (US)

(*) Notice: Subject to any disclaimer, the term of this patent is extended or adjusted under 35 U.S.C. 154(b) by 12 days.

(21) Appl. No.: 12/848,975

(22) Filed: Aug. 2, 2010

(65) Prior Publication Data
US 2010/0298809 A1    Nov. 25, 2010

Related U.S. Application Data

(62) Division of application No. 11/803,925, filed on May 16, 2007, now Pat. No. 7,766,872.

(60) Provisional application No. 60/800,813, filed on May 16, 2006.

(51) Int. Cl.
*A61M 5/00* (2006.01)
*A61M 31/00* (2006.01)
(52) U.S. Cl. ........................ 604/500; 604/110
(58) Field of Classification Search .......... 604/110, 604/187, 192, 198, 500
See application file for complete search history.

(56) References Cited

U.S. PATENT DOCUMENTS 5,135,510 A * 8/1992 Maszkiewicz et al. ....... 604/195
* cited by examiner

*Primary Examiner* — Kevin C Sirmons
*Assistant Examiner* — Bradley Osinski
(74) *Attorney, Agent, or Firm* — Bauman, Dow & Leon, PC; Alberto A. Leon, Esq.

(57) ABSTRACT

The present invention relates to the method of use for a single dose, single use, self-destructing, auto-disabling safety syringe. The invention successfully addresses and solves the problems of the prior art by combining the use of COC injection molding with the advantages presented by the ampoule cartridge and the traditional safety syringe all integrated into a single device. A pre-filled ampoule or barrel is molded with minimal draft enabling the syringe's piston plunger to be partially self-lubricated by the syringe's contents. The addition of an internal auto disabling coupler to the piston plunger allows the device to be used only a single time. In addition, the present invention's structure is such that its safety sleeve necessarily moves forward to cover the syringe's needle after use. The invention's elements solve the biocompatibility and safety problems of the prior art and provide an exact dose, prefilled, single use, safety syringe.

8 Claims, 4 Drawing Sheets

METHOD OF USING PREFILLED, SINGLE DOSE, ONE TIME USE SELF-DESTRUCTING, AUTO-DISABLING SAFETY SYRINGE

CROSS-REFERENCE TO RELATED APPLICATIONS

This application is a divisional patent application from U.S. patent application Ser. No. 11/803,925, now U.S. Pat. No. 7,766,872, filed May 16, 2007 titled "Prefilled, Single Dose, One Time Use, Self-Destructing, Auto-Disabling Safety Syringe With An Injection Molded Barrel; Method Of Manufacture And Method Of Use" by the same inventor and claims priority there from (the "Parent application"). This divisional application is being filed in response to a restriction requirement contained in an office action dated Oct. 24, 2008, and contains the method of use disclosed and claimed in the Parent application, as officially filed, but not elected in applicant's response to the restriction requirement. The Parent application is fully incorporated herein by means of this reference.

The Parent application claims the benefit under Title 35, United States Code Section 119(e) of any U.S. Provisional Application No. 60/800,813 filed on May 16, 2006.

STATEMENT REGARDING FEDERALLY SPONSORED RESEARCH OR DEVELOPMENT

N/A

THE NAMES OF PARTIES TO A JOINT RESEARCH AGREEMENT

N/A

BACKGROUND OF THE INVENTION

1. Field of the Invention

The present invention relates generally to the use of safety hypodermic syringes and, more particularly, but not by way of limitation, to a method of use of a prefilled, single dose, one time use, self-destructing, auto disabling hypodermic syringe with an injection molded barrel.

2. Description of the Related Art (Including Information Disclosed Under 37 C.F.R. 1.97 and 1.98)

The alarming increase of human-fluid borne infectious diseases, their various avenues of spread, and especially, the increase risk of spread due to multiple uses or accidental needle sticks of hypodermic injection systems cannot be ignored.

Over the last twenty years, there have been numerous developments in the field of single dose, prefilled, disposable syringes. U.S. Pat. No. 4,596,561 to Meyer et al., describes and claims a non-reusable syringe comprising a tamper-proof packaging which insures that the proper medication is contained in the barrel, free of any contaminant.

U.S. Pat. No. 5,575,776 to Bleiweiss, discloses and claims a single dose, prefilled, disposable syringe arrangement. The '776 patent's system comprises an outer casing surrounding the syringe in the packaged state, which is collapsible to act as a plunger during use of the syringe. Bleiweiss' patent stresses the single use capability of the syringe, followed by secured disposal and non-reuse.

Pre-filled syringes were originally made from glass or borosilicate. As it is well known in the art, glass structures allow variations in the pH of the contents thus resulting in at least some degradation. Another disadvantage of borosilicate syringes is the need for a medical grade silicone stopper lubricant to advance the plunger. In many cases, silicone tends to break down the contents' proteins thus decreasing the effectiveness of the drug being administered. In addition, injuries from glass syringes and needle-sticks have allowed the spread of blood borne pathogen diseases such as acute or chronic hepatitis, HIV, or AIDS.

In more recent times, some of the problems outlined above have escalated. Caregivers in the hospital, hospice and home-healthcare environments are further exposed to human fluid borne, potentially infectious, diseases while conducting procedures in patients who, due to their condition, may not hold still during an injection. Another potentially dangerous situation takes place if the caregiver drops the syringe accidentally receiving a needle stick or is stuck while cleaning a tray. There have been reported cases where a custodian has received a potentially infectious injury while cleaning the pieces of broken glass from a syringe. Caregiver and worker injuries can significantly increase the costs of medical care as well as insurance for the healthcare facility. All of those costs are usually passed on to the patients.

Healthcare providers are supposed to deposit used syringes in a sharps container immediately after use. Many caregivers place syringes on a tray or cart and injuries can and do occur for failure to follow the proper disposal protocol. Medical device companies have tried to manufacture add on needle stick avoidance devices and spring-loaded covers or shields for the glass syringe. Many of the commercially available devices have unacceptably high failure rates and, in some instances, cannot be securely engaged to the syringe. Most efforts in the stick-avoidance area have taken place in the context of manufacturers trying to assist healthcare providers in compliance with the newly enacted FED/OSHA mandate 29 CFR Part 1910 and European Parliament resolutions; Occupational Exposure to Blood borne Pathogens; Needle sticks and other Sharps Injuries.

Because of the many shortcomings of glass syringes, the next generation of prefilled syringes of the prior art was manufactured using polypropylene. Some polypropylene prefilled syringes of the prior art even had spring-loaded retractable needles, hinged needle guards and flip-over covers. The type of highly clarified polypropylene resin used presented problems in that it posed a risk of leechables and extractables in the resin altering the contents of the medication. In addition, the stopper required a medical grade silicone lubricant to advance the plunger. It is well known in the art that silicone can break down the proteins in the medication, rendering it less effective to the patient. The FDA has denied new drug application approvals of medications being administered via prefilled syringes based on laboratory testing and two-year shelf life restrictions. Accordingly, the safety syringes in the market today are primarily used as general or multi purpose syringes.

Most recently, cyclic olefin copolymer ("COC") has been introduced as the new FDA approved state-of-the-art replacement for glass. COC has excellent barrier properties and is virtually shatterproof. COC also has the look of glass and does not contain crystalline, which makes it as clear as glass. COC is also bio-compatible, so that it does not alter pre-filled medications in the ways polypropylene syringes can. Those characteristics make COC an ideal material to aid overcoming some of the shortcomings of the safety syringe prior art mentioned above.

In the case of COC syringes, many medical manufacturers "blow-mold" the resin into the shape of a syringe component. COC syringes, which lack most, if not all, of the required safety features, present most of the same shortcomings evidenced in the existing art, including needle-sticks and accidental, unintentional or intentional re-use. Furthermore, the COC syringe's stopper still requires a medical grade silicone lubricant to advance the plunger. Again, the silicone can break down proteins in the syringe's content, potentially diminishing the effectiveness of the medication being administered.

COC medical ampoules or blow molded vials are FDA approved and have gained a large percentage of market share. They cannot be blow molded and manufactured as a cartridge because both ends are initially open. During the manufacturing process, the back end is sealed with a piston plunger and the front end is sealed with thermoplastic elastomer ("TPE"), or a rubber seal and an aluminum cap.

Despite prior attempts to comply with FED/OSHA and European Parliament mandates, no compliant, mechanically suitable engineered safety syringe exists for use by the professional caregiver or patient for the safest possible biocompatible safety syringe with anti-needle-stick and auto-disable features. The present invention fulfills all of those requirements and provides an alternative arrangement which effectively addresses and cures all of the shortcomings of the prior art. The present invention is the first pre-filled integrated engineered safety syringe.

In addition, none of the prior art discloses a syringe for doses under 3.0 mL. A small bio-compatible safety syringe is critically needed to address two problems. The first problem is the shortage of refrigerated or temperature-controlled space in most medical settings. A small syringe with a short plunger can help to resolve space issues for low volume vaccines, biologics and allergens. Pediatrics is the second area where a small syringe is needed. A small syringe can accommodate a smaller needle hub and needle. The present invention can be scaled down in length for doses as small as 0.5 mL. A small-sized hub for the smaller syringe is also disclosed.

Applicant's pre-filled syringe invention addresses and solves the problems of the prior art syringes by combining the use of COC injection molding with the advantages presented by the ampoule cartridge and the traditional safety syringe all integrated into a single compliant device. Molding the pre-filled ampoule cartridge with minimal draft enables the plunger to be partially self-lubricated by the syringe's contents and minimizes the use of silicone. The addition of an internal auto disabling coupler to the piston plunger allows the device to be used only a single time. In addition, the applicant's syringe invention comprises opposing tabs at the proximal end, a universal hub attached to the distal end, and an integrated safety sleeve with forward mounted opposing tabs.

BRIEF SUMMARY OF THE INVENTION

The structural arrangement of Applicant's syringe invention allows the sleeve to move only in a forward direction and lock in all forward positions to cover the needle. Once the sleeve is locked in the forward position, where it encapsulates the needle, it is no longer possible to retract it and expose the needle. Any attempt to forcibly expose the needle once encapsulated, results in the sleeve and the needle hub disengaging from the cartridge barrel as a single unit. The method of the present invention then allows the use of a truly hybrid syringe in that the syringe can be pre-filled or general purpose; it can accommodate universal hubs or luer hubs; and it can be manufactured in small sizes for low dose and pediatric use. The inventive elements of the present invention, as combined, solve the biocompatibility, size and safety problems of the methods of the prior art and provide an exact dose, prefilled, single time use, cartridge safety syringe.

DETAILED DESCRIPTION OF THE INVENTION

Figure 1:
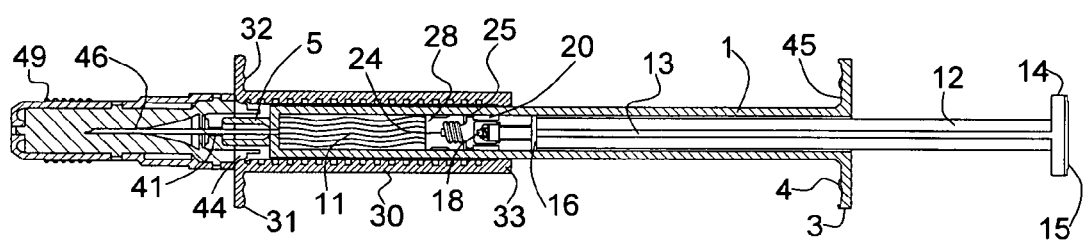
FIG. 1 is a frontal view of the fully assembled preferred embodiment of the invention.
Figure 2:
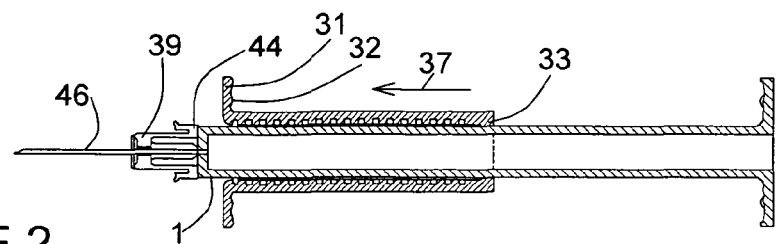
FIG. 2 is a frontal view of the sleeve and hub attached to the barrel.
Figure 3:
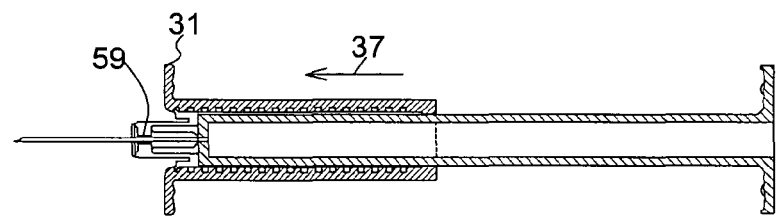
FIG. 3 is a frontal view of the sleeve snap-assembled to the hub in the first locking position.

Structurally, the single use, self-destructing, safety syringe of the applicant's syringe invention comprises an injection molded COC ampoule cartridge syringe barrel (1) suitable for receiving an injectable liquid. The barrel comprises opposite proximal and distal ends, an outer surface and an inner surface. The proximal end is open and is capable of receiving a plunger (12). The barrel is molded so that the proximal end extends into two opposing tabs (3) perpendicular to the barrel. Each tab comprises an ergonomic radius section (45) following extension point of the tab from the barrel, continuing into a single standing rib (4) for comfortable, non-slip use. A recessed well (10) is located on the outer surface between the two opposing tabs, the well comprising a droplet of ink or a label with ink, capable of acting as a sterilization indicator. The indicator can be selective (such as gamma) or multi-process (such as E-beam). The indicator can be colorless and change to a color or can be a color that changes to another color when sterilization is compromised. The opening (2) in the proximal end is capable of engaging an auto-disabling coupling subassembly which is further connected to the stopper (29). The inner surface of the distal end of the barrel comprises three forward positioned internal flat ribs (8) so that an interference (9) with the coupling sub-assembly is created allowing the release of the coupling sub-assembly upon moving the plunger forward and completing the administration of the syringe's contents. The distal end further comprises an opening (6) and a universal receiving neck (5). The neck comprises an interior and an exterior, the interior comprising an internal retention rib (7) for connection of the male needle hub (39) to the ampoule cartridge syringe barrel (1). The outer surface of the barrel is capable of receiving a printed DNA ink identification to identify its content as an anti-counterfeit drug measure. Alternately, a DNA ink tear-off label can be affixed to the barrel. The tear-off label can be attached to a patient's charts after drug administration to help track administration of drugs.

The stopper (29) is made from non-reactive compression molded thermoplastic elastomer, and comprises a piston-shaped exterior and a flat distal end. The stopper's configuration significantly reduces the dead space volume in the ampoule cartridge barrel. The proximal end comprises a threaded female receiving opening for screw-insertion of the coupler's forward male threaded end (24). The pre-filled medication (11) is contained in the barrel between the stopper and the barrel's neck.

The coupler (22) is made from polypropylene. It comprises a forward male threaded end (24), an increased diameter circular standing flat rib (25) and a rear female end. The threaded male forward end (24) comprises a centered protrusion and is capable of being screw-inserted into the stopper's threaded female receiving end (29) and being locked firmly into place by turning the male forward end 360 degrees clockwise. The increased diameter standing flat rib (25) is capable of passing the barrel's internal flat ribs, seating the stopper and allowing the stopper to advance to a fully extended distal position in the barrel. The rear female end of the coupler diameter is reduced and comprises and internally threaded receiving means (27) and four longitudinally split side arms (26), the side arms comprising multiple standing flex fingers capable of engaging the coupler ring (19) through snap-assembly. The coupler is capable of aspirating proximally and distally inside the barrel as part of an interconnected assembly. The coupler is further capable of interacting with the barrel's internal flat ribs (8) to allow the release of the coupler upon completion of the administration of the syringe's contents.

The cylindrical coupler ring is designed to have a large diameter wall thickness (21) that does not allow the ring to flex. The coupler ring is capable of being snap-assembled over the coupler's side arms to create an inside dimension interference (20) which maintains the coupler and ring assembly in place.

The plunger (12) is made from polypropylene or COC and comprises a cylindrical shaft, the shaft being smaller in diameter than the barrel, the shaft comprising opposite proximal and distal ends. The distal end is circular so it can be received by and be inserted into the barrel's proximal end opening. The proximal end ends in a cylindrical disk (14), the disk comprises a circular raised rib (15) along the exterior of the disk's diameter and an embossed logo to frictionally reduce slippage. The shaft of the plunger is X-braced (13) to a forward positioned standing raised rib (16) that approximates the inner diameter of the barrel and self centers the plunger along the inside diameter of the cartridge barrel. The plunger's distal end comprises a reduced diameter section near the distal end to allow space for the coupler ring (19) to disengage from the plunger. The plunger's distal end further comprises a self-centering threaded male end (18) being capable of being inserted through the coupler ring and firmly snap-fitting into the coupler's threaded receiving means. The plunger is capable of releasing the coupler upon moving the plunger forward, after administration of the syringe's contents. In an alternative embodiment of the invention, wherein the syringe is not prefilled, the plunger's shaft is longer to allow a dose to be drawn from a separate container.

The self-disabling coupling sub-assembly interconnects the stopper (29), the coupler (22), the coupler ring (19), and the plunger (12), which is snap-assembled into a single unit. The sub-assembly is inserted into the proximal end of the cartridge barrel (1) after the barrel is pre-filled with medication. The internal coupling sub-assembly aspirates proximally and distally inside the cartridge barrel as one interconnected assembly. When the stopper, coupler and coupler ring are advanced by the plunger to a distal position, the coupler ring interference (20) engages the three flat ribs (8) of the cartridge barrel releasing the coupler ring (19) from the coupler (22), allowing the flex fingers to expand, which in turn creates an interference from the stopper (29) against the flat ribs of the cartridge and allows the coupler's flex fingers (26) to disengage from the plunger, rendering it useless for re-injection. The coupler subassembly is capable of pushing the single dose of medication located in the barrel between the barrel's neck and the stopper out of the barrel through the barrel's neck when the plunger is advanced to a distal position in the barrel.

A plunger cap (57) such as that used in an all-purpose syringe can be used with the syringe of this invention to create a dynamic interface triple seal lock (58) and a complete sterile internal environment.

A male staked needle hub (39) is made from polypropylene and is engaged to the barrel's universal receiving neck (5) by a male snap insertion and is held in place by the undercut of the male hub and the standing internal retention rib (7) of the barrel's neck. The hub comprises a uniform internal surface (42) that aligns with the exterior of the cartridge neck creating a uniform surface interference for snap assembly. The hub further comprises opposing dual flex fingers (44) that lock into the sleeve's opposing locks (35) for anti-needle stick protection. The hub also comprises dual opposing flat ribs (43) that allow the sleeve to move distally and dual opposing flex fingers (44) that lock the sleeve in all forward positions, protecting the caregiver from the needle as the sleeve extends distally past the needle into a fully extended distal position. The hub also comprises an extended forward end with three raised ribs (40) that create a sterile barrier when connected to the needle cap/sheath (47). The hub further comprises a dimple (41) at the forward end with UV-cured adhesive and spiral relief dimensional undercuts and a center opening (53) with low dead space that create a mechanical lock (59) when a hollow needle (46) or cannula lumen is inserted and adhered to through the center opening of the hub.

Figure 4:
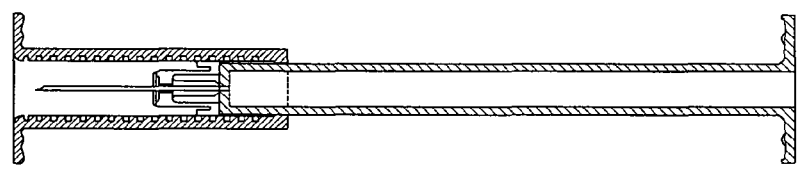
FIG. 4 is a frontal view of the sleeve fully extended to the distal position, encapsulating the hub and needle.
Figure 5:
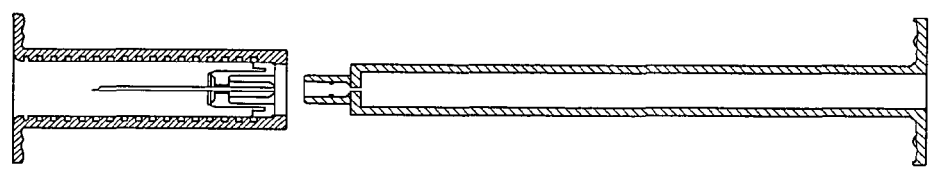
FIG. 5 is a frontal view of the sleeve removed from cartridge barrel, encapsulating the hub and needle.
Figure 6:
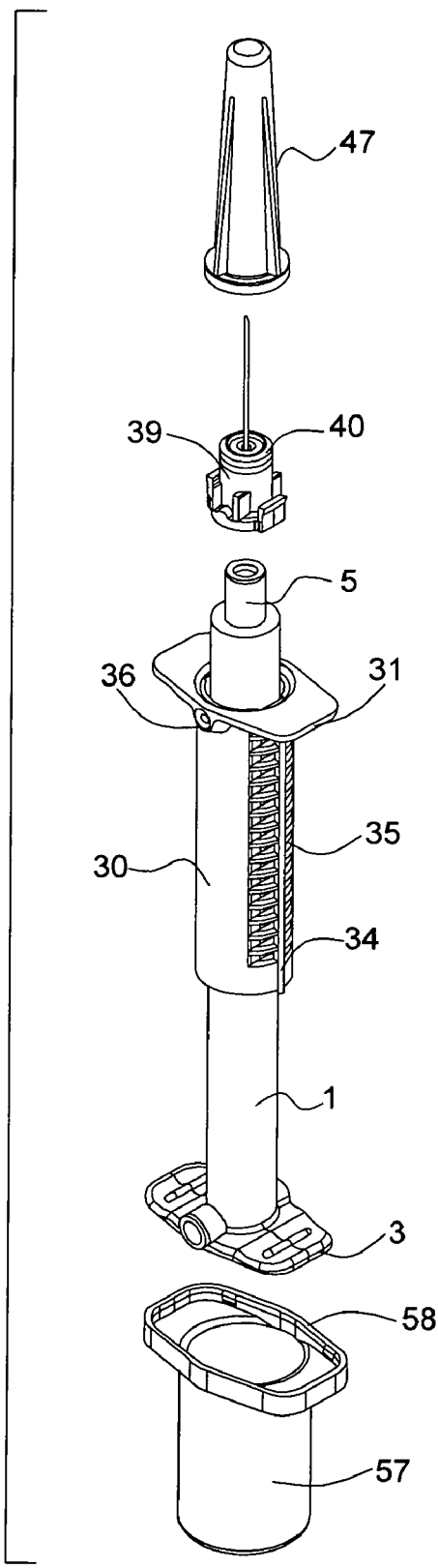
FIG. 6 is an isometric exploded view of the preferred embodiment of the invention.

An elliptical shaped sleeve (30) made from COC cyclic olefin copolymer is capable of sliding over the cartridge barrel (1) and snap assembling to the needle hub (39). The length of the sleeve varies depending on the length of the needle that will be used with the syringe, so that the sleeve is capable of completely encapsulating the needle. The sleeve comprises an inner side, an outer side, an open proximal end, an open distal end, and two opposing series of horizontal locking slats (35). The two opposing series of horizontal locking slats extend from the proximal end to the distal end and have rectangular holes that extend from the inner side to the outer side between the slats. The slats are capable of engaging the hub's flex fingers (44), this engagement resulting in the slats being oriented ninety degrees away from the needle hub's dual opposing flat ribs (43) and the sleeve and the hub being locked together. The hub's flex fingers (44) are capable of locking onto any of the slats in forward distal positions as the sleeve is advanced. The flex fingers prevent the sleeve from moving proximally, so that only distal advancement is possible (37). Distal advancement of the sleeve results in anti-needle stick protection as the sleeve is longer than the needle and is capable of extending past the needle, encapsulating it, as is shown in FIG. 4. The inner side of the proximal end comprises interference shelves (33) capable of irreversibly engaging the needle hub when the sleeve is extended past the locking slats to a fully distal position. When the sleeve is advanced to its forward-most distal position, the interference shelves (33) at the proximal end of the sleeve firmly lock onto the needle hub in such a way that the sleeve can not be advanced further. Any attempt to further advance the sleeve will result in the hub disengaging from the barrel's receiving neck, as pictured in FIG. 5, resulting in complete needle stick protection for any person subsequently handling the syringe or its parts. The outer side comprises a bio-indicator (36) and a raised rib (34) extending along the center of each set of locking slats, the raised ribs being perpendicular to the slats. The bio-indicator provides additional identification regarding the syringe or its contents. In alternative embodiments, the bioindicator can be located on the barrel. The distal end of the sleeve is molded so that the distal end extends into two opposing tabs (31) perpendicular to the sleeve, each tab comprising an ergonomic radius section following the extension point of the tab from the sleeve, continuing into a single standing rib (32) for comfortable non-slip use. The tabs being capable of being rotated axially (38) when the sleeve is engaged with the hub flex fingers (44), allowing for the correct needle bevel (60) orientation for injection. Upon a completed administration of the syringe's contents, the user holds the sleeve's tabs (31) and withdraws the barrel tabs (3), encapsulating the needle without ever exposing the needle. The sleeve's elliptical shape is capable of creating a lens effect, resulting in 100 percent visibility of the contents in the barrel being administered.

The needle cap (47) comprises an exterior shell, an interior, an engaging end and a closed end. The exterior shell is made of high-impact polypropylene that is impervious to the tip of the needle. The cap's interior comprises a soft thermoplastic elastomer (50) capable of engaging the needle. Surrounding the needle with TPE prevents leakage of the pre-filled barrel's contents through the needle. The engaging end is capable of firmly engaging the three standing coaxial ribs (40) on the needle hub's extended forward end in such a way that a sterile environment is created in the space between the needle and the cap, and keeping the cap in place. The cap further comprises four standing coaxial ribs (49) extending horizontally around the outer circumference of the closed end, being capable of creating a non-slip grip for ease of removal of the cap from the hub.

In an alternative embodiment of Applicant's syringe invention, illustrated by FIGS. 21 and 22 of the Parent Application, the universal hub is interchangeable from a staked hub to a luer hub (51) during assembly, allowing for the choice of needle/lumen for the proper procedure. The luer hub comprises flex fingers (54) capable of engaging the sleeve in all forward positions. The luer hub further comprises a two-part cap (55) made of polypropylene and TPE thermo plastic elastomer with a threaded base (56). The threaded base corresponds to threads on the luer hub (52). The screw tightening of the two-part cap compresses the TPE seal creating a sterile barrier.

In an alternative embodiment of Applicant's syringe invention, the length of the syringe is scaled-down to accommodate a small dose between 0.5 and 3.0 mL and a small universal needle hub is used instead of the hub of the preferred embodiment. The small universal hub is illustrated by FIGS. 18 and 19 of the Parent Application. The small hub comprises smaller flex fingers (45) and dual opposing linear ribs (43) for accommodating a smaller sleeve. This smaller embodiment addresses the need for small-sized safety syringes for limited space, low doses and pediatric applications.

Figure 7:
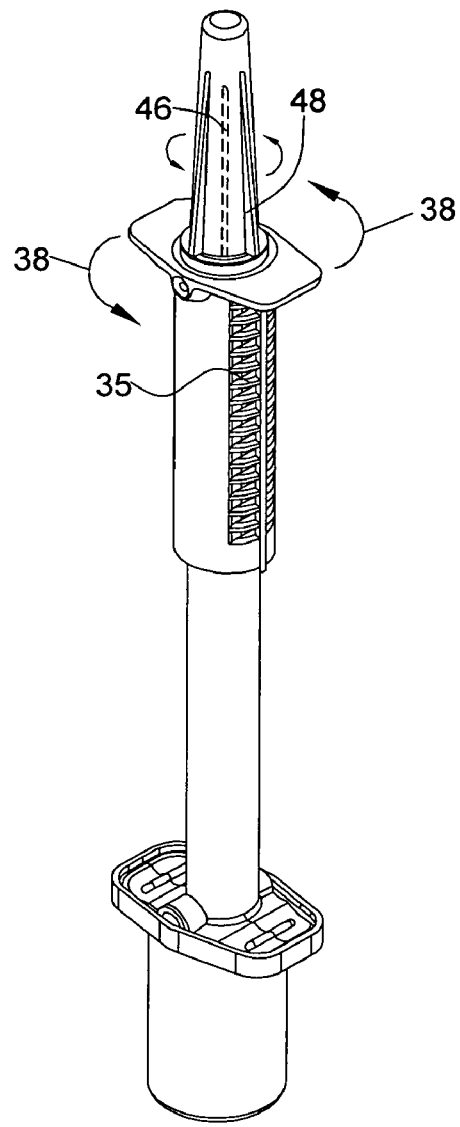
FIG. 7 is an isometric view of the preferred embodiment of the invention.
Figure 8:
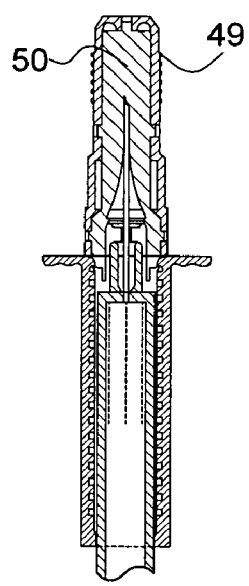
FIG. 8 is a frontal view of the needle cap on the syringe in the preferred embodiment of the invention.
Figure 9:
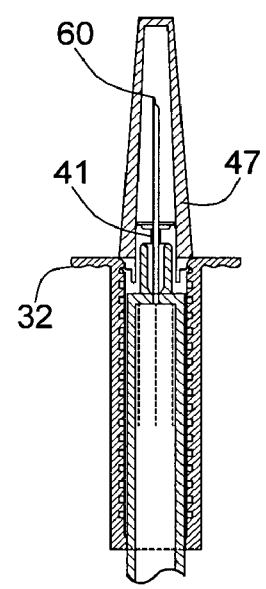
FIG. 9 is a frontal view of a standard needle cap on the syringe in the general purpose alternative embodiment of the invention.

In an alternative embodiment of Applicant's syringe invention for general purpose use, the syringe is not pre-filled with medication. The dose is drawn into the syringe through the needle from a separate medicine vial. The plunger is longer to allow for medication to be withdrawn from a medicine vial. The syringe coupler sub-assembly parts are different, as pictured in FIG. 7 of the Parent Application, to allow for quick assembly for high volume automated manufacture. The plunger (12) comprises a male chamfered forward distal end (18) for snap insertion into the female chamfered end (27) of the coupler. The coupler comprises a female chamfered end (27) and a male chamfered forward end (23). The stopper (28) comprises a female chamfered end that engages the male chamfered forward end of the coupler. The standard needle cap/sheath is used for the general purpose embodiment, as is pictured in FIG. 9. The standard needle cap comprises four standing tapered ribs (48) extending vertically, allowing for non-slip removal of the cap from the syringe. This general purpose embodiment can incorporate other alternative embodiments, such as the luer hub or low dose size, resulting in a hybrid syringe with maximum functional flexibility.

The method of using the pre-filled safety syringe of this invention comprises the steps of: (1) removing the syringe from a sterile blister package; (2) removing the needle cap; (3) aligning the needle for proper use by rotating the sleeve; (4) administering the syringe's contents to the patient via injection by depressing the plunger to a full distal position for completed injection; (5) holding the forward sleeve tabs; (6) pulling back the rear cartridge barrel tabs which results in encapsulating the hub and needle into the sleeve; (7) allowing the internal coupler to disengage automatically which results the plunger being released form the internal coupler, resulting in a syringe which cannot be re-used accidentally or intentionally under any conceivable set for circumstances; and (8) placing the spent device in a sharps container.

The structural features of the syringe of Applicant's syringe invention can only be achieved due to the horizontal molding COC manufacturing process. The internal components are male to female interconnected or screw fit and are inserted into the proximal end of the cartridge barrel. The sleeve is slid over the cartridge and the hub, needle, and sheath are snap-assembled to a universal neck at the distal end of the cartridge barrel. The automatic snap assembly feature of the present invention can only be achieved via the design relationship of same axis centerline part design. The centerline snap assembled components are designed for high-speed sterile assembly. The coupler, coupler ring, hub and other polypropylene parts can be tinted for color-coding to indicate the type of medication, patient or other use for that syringe.

What I claim is:

1. A method of using a prefilled, single dose, one time use, auto-disabling, self-destructing, safety syringe, comprising the steps of:
  a. providing a prefilled, single dose, one time use, auto-disabling, self-destructing, safety syringe comprising a barrel, the barrel further comprising multiple barrel tabs, a sleeve, the sleeve further comprising multiple sleeve tabs and opposing horizontal locking slats, a plunger capable of being manually depressed to a full distal position or completed injection position, a hub, the hub further comprising flex fingers capable of engaging the sleeve's locking slats, a coupler, the coupler further comprising an internal coupling, a coupler ring and a coupling sub-assembly, a needle and a needle cap, the syringe being capable of being contained in a sterile blister package;
  b. removing the syringe from the sterile blister package;
  c. removing the syringe's needle cap;
  d. orienting the syringe's needle by twisting the sleeve tabs;
  e. administering the syringe's contents to a patient via injection by depressing the syringe's plunger to a full distal position or completed injection position;
  f. holding the syringe's sleeve tabs;
  g. pulling back the syringe's barrel tabs resulting in encapsulating the syringe's hub and needle into the syringe's sleeve without the needle ever being exposed after administration of the syringe's contents;

h. allowing the syringe's coupling sub-assembly to disengage automatically resulting in the syringe's plunger being released from the syringe's internal coupler, further resulting in the syringe not being capable of being reused accidentally or intentionally under any conceivable set of circumstances; and i. placing the used syringe in a sharps container.

2. The method of using a prefilled, single dose, one time use, auto-disabling, self-destructing, safety syringe of claim 1 wherein the syringe is capable of being used for administration of low doses of medication.

3. The method of using a prefilled, single dose, one time use, auto-disabling, self-destructing, safety syringe of claim 1 wherein the syringe's universal hub is interchangeable from a staked hub to a luer hub during assembly, allowing for the choice of needle/lumen adaptable to the specific dose administration being performed.

4. The method of using a prefilled, single dose, one time use, auto-disabling, self-destructing, safety syringe of claim 1 wherein the coupler, coupler ring, hub and other polypropylene parts are manufactured so they provide for color-coding to indicate the type of medication, patient or other use for the syringe.

5. A method of using a single dose, one time use, auto-disabling, self-destructing, safety syringe, comprising the steps of:

a. providing a single dose, one time use, auto-disabling, self-destructing, safety syringe comprising a barrel, the barrel further comprising multiple barrel tabs, a sleeve, the sleeve further comprising multiple sleeve tabs and opposing horizontal locking slats, a plunger capable of being manually depressed to a full distal position or completed injection position, a hub, the hub further comprising flex fingers capable of engaging the sleeve's locking slats, a coupler, the coupler further comprising an internal coupling, a coupler ring and a coupling sub-assembly, a needle and a needle cap, the syringe being capable of being contained in a sterile blister package;

b. removing the syringe from the sterile blister package;

c. removing the syringe's needle cap;

d. drawing a dose of medication into the syringe through the needle from a separate medicine vial;

e. orienting the syringe's needle by twisting the sleeve tabs;

f. administering the syringe's contents to a patient via injection by depressing the syringe's plunger to a full distal position or completed injection position;

g. holding the syringe's sleeve tabs;

h. pulling back the syringe's barrel tabs resulting in encapsulating the syringe's hub and needle into the syringe's sleeve without the needle ever being exposed after administration of the syringe's contents;

i. allowing the syringe's coupling sub-assembly to disengage automatically resulting in the syringe's plunger being released from the syringe's internal coupler, further resulting in the syringe not being capable of being reused accidentally or intentionally under any conceivable set of circumstances; and j. placing the used syringe in a sharps container.

6. The method of using a single dose, one time use, auto-disabling, self-destructing, safety syringe of claim 5 wherein the syringe is capable of being used for administration of low doses of medication.

7. The method of using a single dose, one time use, auto-disabling, self-destructing, safety syringe of claim 5 wherein the syringe's hub is interchangeable from a staked hub to a luer hub during assembly, allowing for the choice of needle/lumen adaptable to the specific dose administration being performed.

8. The method of using a single dose, one time use, auto-disabling, self-destructing, safety syringe of claim 5 wherein the coupler, coupler ring, hub and other polypropylene parts are manufactured so they provide for color-coding to indicate the type of medication, patient or other use for the syringe.

* * * * *